US012594048B2

(12) United States Patent (10) Patent No.: US 12,594,048 B2
Ye (45) Date of Patent: Apr. 7, 2026

(54) NOISE ANALYSIS SYSTEMS AND METHODS

(71) Applicant: SHANGHAI UNITED IMAGING HEALTHCARE CO., LTD., Shanghai (CN)

(72) Inventor: Yongquan Ye, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 320 days.

(21) Appl. No.: 18/327,018

(22) Filed: May 31, 2023

(65) Prior Publication Data

US 2023/0380789 A1 Nov. 30, 2023

(30) Foreign Application Priority Data

May 31, 2022 (CN) .......................... 202210606176.6

(51) Int. Cl.
| | |
|---|---|
| *G06T 7/00* | (2017.01) |
| *A61B 5/055* | (2006.01) |
| *A61B 6/00* | (2006.01) |
| *G06T 5/70* | (2024.01) |

(52) U.S. Cl.
CPC .......... *A61B 6/5258* (2013.01); *G06T 7/0012* (2013.01); *G06T 2207/10088* (2013.01); *G06T 2207/30168* (2013.01)

(58) Field of Classification Search
None
See application file for complete search history.

(56) References Cited

U.S. PATENT DOCUMENTS

| | | | |
|---|---|---|---|
| 6,388,441 B1 | 5/2002 | Chen | |
| 2010/0086184 A1 | 4/2010 | Krüger et al. | |
| 2011/0105884 A1 | 5/2011 | Beck | |
| 2017/0172453 A1* | 6/2017 | Madore | G01R 33/50 |
| 2018/0081004 A1 | 3/2018 | Yang | |
| 2018/0143272 A1 | 5/2018 | Liu | |
| 2018/0338701 A1 | 11/2018 | Amemiya et al. | |
| 2020/0037918 A1* | 2/2020 | Sakashita | G06T 5/50 |
| 2020/0090382 A1 | 3/2020 | Huang et al. | |
| 2020/0300951 A1* | 9/2020 | Ye | G01R 33/561 |
| 2020/0302605 A1* | 9/2020 | Ye | G06T 7/0014 |

(Continued)

FOREIGN PATENT DOCUMENTS

| | | | | |
|---|---|---|---|---|
| CN | 108802648 | * | 11/2018 | G01R 33/5602 |
| CN | 113050010 | * | 6/2021 | A61B 6/5241 |

OTHER PUBLICATIONS

Ajay Kumar Boyat et al., A Review Paper: Noise Models in Digital Image Processing, Signal & Image Processing: An International Journal, 6(2): 63-75, 2015.

(Continued)

*Primary Examiner* — Beniyam Menberu
(74) *Attorney, Agent, or Firm* — METIS IP LLC

(57) ABSTRACT

A method and a system for noise analysis may be provided. A plurality of signals of a target object may be obtained. A first value of a first signal representation and a second value of a second signal representation of the target object may be determined based on the plurality of signals. A value of a noise parameter may be determined based on the first value of the first signal representation and the second value of the second signal representation.

20 Claims, 9 Drawing Sheets

100

(56) References Cited

U.S. PATENT DOCUMENTS

| | | | |
|---|---|---|---|
| 2020/0303049 A1 | 9/2020 | Zhang et al. | |
| 2020/0371184 A1 * | 11/2020 | Ye | G01R 33/5659 |

OTHER PUBLICATIONS

Ye, Yongquan et al., A Mulli-Dimensional Integration (MDI) Strategy for MR T2* Mapping, NMR in Biomedicine, 2021, 15 pages.
Sebastian Bidhult et al., Validation of a New T2* Algorithm and Its Uncertainty Value for Cardiac and Liver Iron Load Determination from MRI Magnitude Images, Magnetic Resonance in Madicine, 75: 1717-1729, 2016.
Tobias Hesper et al., T2* Mapping for Articular Cartilage Assessment: Principles, Current Applications, and Future Prospects, Skeletal Radiol, 43: 1429-1445, 2014.
Wu, Bing et al., Fast and Tissue-Optimized Mapping of Magnetic Susceptibility and T2+ with Multi-Echo and Multi-Shot Spirals, Neuroimage, Author Manuscript, 2012, 21 pages.

* cited by examiner

100

<u>400</u>

810                              820

NOISE ANALYSIS SYSTEMS AND METHODS

CROSS-REFERENCE TO RELATED APPLICATIONS

This application claims priority to Chinese Patent Application No. 202210606176.6, filed on May 31, 2022, the contents of which are hereby incorporated by reference.

TECHNICAL FIELD

The present disclosure relates to medical imaging technology, and in particular, to systems and methods for noise analysis in medical imaging.

BACKGROUND

In medical imaging field, noise analysis needs to be performed on imaging data to improve imaging quality. In general, noise analysis is normally performed based on real signals. Complex signals such as signals obtained by a magnetic resonance imaging (MRI) device need to be decomposed into real and imaginary parts, or amplitude and phase, and the noise analysis is performed on the amplitude part, which is also a real signal. A signal-to-noise ratio (SNR) is often used to measure an impact of noise on a signal, which refers to a ratio between signal intensity (amplitude) and noise variance. When the noise variance is calculated, a statistical analysis needs to be performed on a plurality of points distributed spatially or temporally, which may be in accurate or difficult to realize. For example, when the plurality of points in space are analyzed, the plurality of points have different signal strengths, leading to a signal intensity not equivalent to the noise variance; when signal values of a same space point at different time points are obtained by repeating signal acquisitions over time, although the signal intensity is equal to the noise variance in this case, the acquisition operation needs to be performed repeatedly. In addition, after a mathematical operation is performed on the signal, the noise performance may change, which may increase the difficulty of noise analysis and affect the accuracy of noise analysis.

Therefore, it is desired to provide methods and systems for noise analysis.

SUMMARY

According to an aspect of the present disclosure, a method for noise analysis may be provided. The method may be implemented on at least one processor. The method may include obtaining a plurality of signals of a target object. The method may also include determining a first value of a first signal representation and a second value of a second signal representation of the target object, based on the plurality of signals. The method may further include determining a value of a noise parameter based on the first value of the first signal representation and the second value of the second signal representation.

In some embodiments, the first signal representation and the second signal representation may be defined as reciprocal with respect to each other.

In some embodiments, the plurality of signals may at least include a first group of images and a second group of images. To obtain plurality of signals of the target object, the method may include the following operations. The method may include collecting the first group of images by instructing a magnetic resonance imaging (MRI) device to perform a first acquisition on the target object. The method may further include collecting the second group of images by instructing the MRI device to perform a second acquisition on the target object.

In some embodiments, the first group of images and the second group of images may correspond to different values in a first target signal dimension.

In some embodiments, the first target signal dimension may be a repetition dimension, and the first acquisition and the second acquisition may be performed by applying a same pulse sequence in different scans.

In some embodiments, the first target signal dimension is an echo time (TE) dimension, and the first acquisition and the second acquisition may be performed by applying a multi-echo sequence in a single scan.

In some embodiments, the first group of images may include a plurality of first images correspond to different values in at least one second target signal dimension, and the second group of images may include a plurality of second images correspond to different values in the at least one second target signal dimension.

In some embodiments, the MRI device may include a plurality of coil channels, and the at least one second target signal dimension may at least include a coil channel dimension.

In some embodiments, to determine the first value of the first signal representation and the second value of the second signal representation based on the plurality of signals, the method may include determining the first value of the first signal representation and the second value of the second signal representation using a multi-dimensional integration (MDI) algorithm.

In some embodiments, the first value of the first signal representation may be an absolute value of the first signal representation, the second value of the second signal representation may be an absolute value of the second signal representation, and to determine a first value of a first signal representation and a second value of a second signal representation of the target object based on the plurality of signals, the method may include the following operations. The method may include, for each of the plurality of coil channels, determining a first product of a conjugate image of the second image corresponding to the coil channel and the first image corresponding to the coil channel, a second product of a conjugate image of the first image corresponding to the coil channel and the second image corresponding to the coil channel, a third product of the conjugate image of the second image corresponding to the coil channel and the second image corresponding to the coil channel, and a fourth product of the conjugate image of the first image corresponding to the coil channel and the first image corresponding to the coil channel. The method may also include designating a ratio of a sum of the first products of the plurality of coil channels to a sum of the third products of the plurality of coil channels as the first value of the first signal representation. The method may further include designating a ratio of a sum of the second products of the plurality of coil channels to a sum of the fourth products of the plurality of coil channels as the second value of the second signal representation.

In some embodiments, to determine a value of a noise parameter based on the first value of the first signal representation and the second value of the second signal representation, the method may include designating a product of the first value of the first signal representation and the second value of the second signal representation as the value of the noise parameter.

In some embodiments, the noise parameter may reflect a signal-to-noise ratio (SNR) of the plurality of signals.

In some embodiments, the plurality of first images and the plurality of second images may be complex images.

According to another aspect of the present disclosure, a system for noise analysis may be provided. The system may include at least one storage device including a set of instructions and at least one processor in communication with the at least one storage device. When executing the set of instructions, the at least one processor may be configured to direct the system to perform the following operations. The systems may obtain a plurality of signals of a target object. The system may also determine a first value of a first signal representation and a second value of a second signal representation of the target object based on the plurality of signals. Further, the system may determine a value of a noise parameter based on the first value of the first signal representation and the second value of the second signal representation.

According to another aspect of the present disclosure, a non-transitory computer readable medium may be provided. The non-transitory computer readable medium may comprise at least one set of instructions for noise analysis. When executed by one or more processors of a computing device, the at least one set of instructions may cause the computing device to perform a method. The method may include obtaining a plurality of signals of a target object. The method may also include determining a first value of a first signal representation and a second value of a second signal representation of the target object, based on the plurality of signals. The method may further include determining a value of a noise parameter based on the first value of the first signal representation and the second value of the second signal representation.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
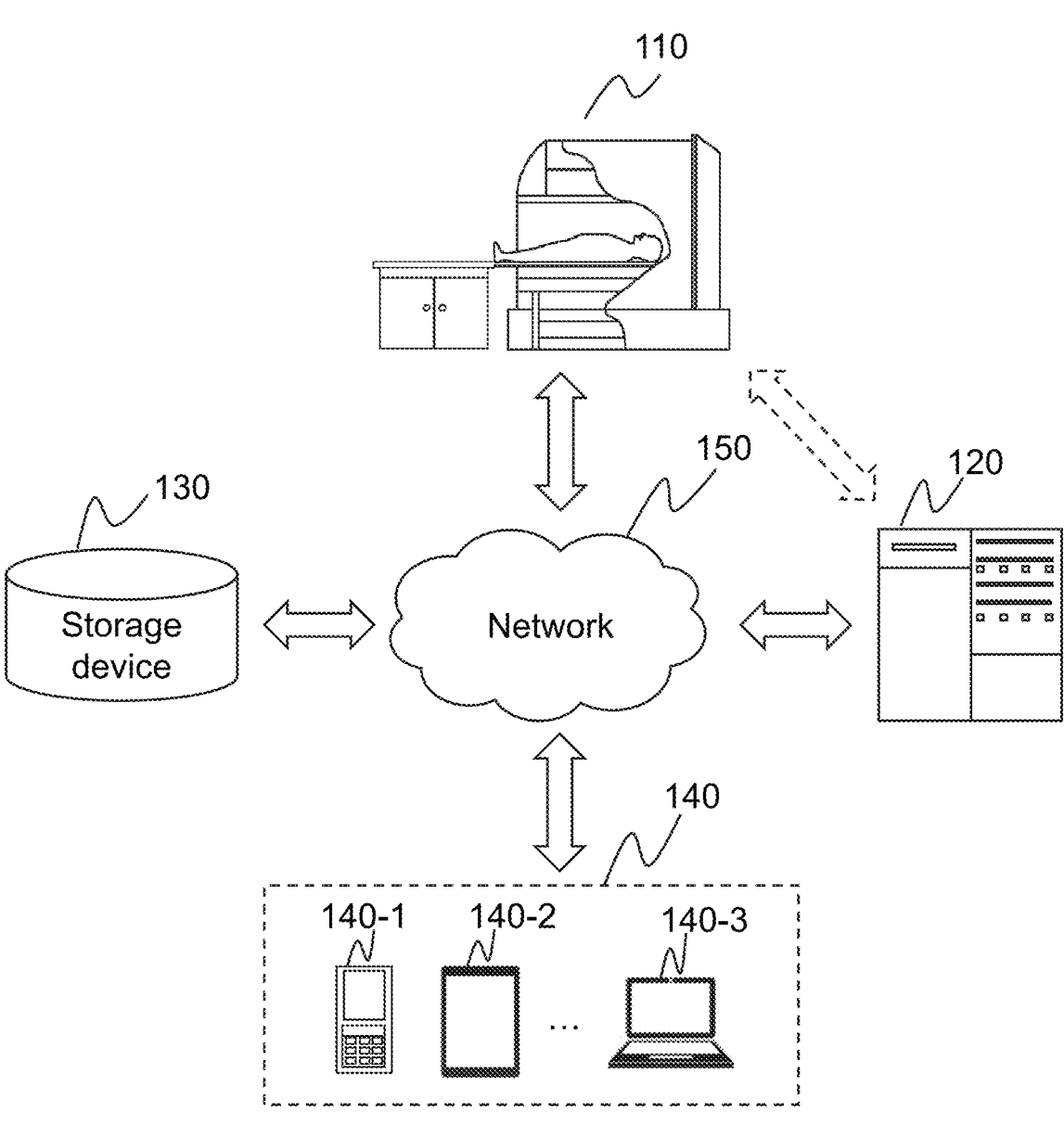
FIG. 1 is a schematic diagram illustrating an exemplary noise analysis system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The term "pixel" and "voxel" in the present disclosure are used interchangeably to refer to an element of an image. An anatomical structure shown in an image of a subject (e.g., a patient) may correspond to an actual anatomical structure existing in or on the subject's body. The term "object" and "subject" in the present disclosure are used interchangeably to refer to a biological object (e.g., a patient, an animal) or a non-biological object (e.g., a phantom). In some embodiments, the object may include a specific part, organ, and/or tissue of the object. For example, the object may include the head, the bladder, the brain, the neck, the torso, a shoulder, an arm, the thorax, the heart, the stomach, a blood vessel, soft tissue, a knee, a foot, or the like, or any combination thereof, of a patient.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

As aspect of the present disclosure provides systems and methods for noise analysis. The systems may obtain a plurality of signals of a target object. The systems may determine a first value of a first signal representation and a second value of a second signal representation of the target object based on the plurality of signals. In some embodiments, the first value of the first signal representation and the second value of the second signal representation may be defined as reciprocal with respect to each other. Further, the systems may determine a value of a noise parameter based on the first value of the first signal representation and the second value of the second signal representation. The noise parameter may reflect an SNR of the plurality of signals.

The noise analysis methods of the present disclosure may directly perform the noise analysis on complex signals, which may avoid the effect of the conversion of complex signals to real signals on the noise analysis, which may improve the accuracy of noise analysis and reduce the difficulty of noise analysis. Moreover, the noise analysis methods of the present disclosure do not need to introduce a disturbance signal, which can reduce the operation difficulty and simplify the analysis process.

In some application scenarios, a noise analysis system may include a processing device and a medical imaging device (e.g., an MRI device, etc.). The medical imaging device may be used to collect a signal, the processing device may be used to implement methods and/or processes disclosed in the present disclosure to perform noise analysis on the signal collected by the medical imaging device. Further, the processing device may perform a noise reduction processing on the signal collected by the medical imaging device based on the noise analysis result to obtain a corrected signal.

FIG. 1 is a schematic diagram illustrating an exemplary noise analysis system according to some embodiments of the present disclosure.

As shown in FIG. 1, in some embodiments, the noise analysis system 100 may include a medical imaging device 110, a processing device 120, a storage device 130, a terminal 140, and a network 150.

The medical imaging device 110 may obtain imaging data (also referred to as "signal") relating to a target object by scanning the target object. The imaging data may include raw data (e.g., projection data, an MRI echo signal, etc.) and/or data generated based on the raw data (e.g., K-space data, an image, etc.). The medical imaging device 110 may refer to a medical device that uses different media to reproduce an internal structure of a human body into an image, such as a digital imaging device, an X-ray computed tomography device, an MRI device, a positron emission tomography device, a nuclear medicine imaging device, or the like. In some embodiments, the medical imaging device 110 may be an MRI device. For illustration purposes, the present disclosure may describe the MRI device as an example. It should be understood that this example is only provided for illustrative purposes and not to limit the scope of protection.

In some embodiments, the medical imaging device 110 may transmit collected imaging data to the processing device 120. The medical imaging device 110 may receive an instruction sent by a doctor through the terminal 140 and perform related operations according to the instruction, such as scanning a subject, or the like. In some embodiments, the medical imaging device 110 may exchange data and/or information with other components (e.g., the processing device 120, the storage device 130, or the terminal 140) of the noise analysis system 100 through the network 150. In some embodiments, the medical imaging device 110 may connect with other components in the noise analysis system 100 directly. In some embodiments, one or more components (e.g., the processing device 120, the storage device 130) in the noise analysis system 110 may be included in the medical imaging device 110.

The processing device 120 may process data and/or information obtained from other components of the noise analysis system 100 to perform the noise analysis methods disclosed herein. For example, the processing device 120 may determine a signal ratio (e.g., a first signal ratio and/or a second signal ratio) based on a plurality of signals of a target object collected by the medical imaging device 110 and determine a noise parameter based on the signal ratio. As another example, the processing device 120 may correct the plurality of signals of the target object based on the determined noise parameter to suppress noises in the plurality of signals. In some embodiments, the processing device 120 may send the processed data such as the signal ratio, the noise parameter, the corrected signals, etc., to the storage device 130 for storage. In some embodiments, the processing device 120 may obtain pre-store data and/or information from the storage device 130, such as the signal ratio and/or noise parameter, the plurality of signals of the target object collected by the medical imaging device 110, or the like, to perform the noise analysis methods illustrated in some embodiments of the present disclosure.

In some embodiments, the processing device 120 may include one or more sub-processing devices (e.g., a single core processing device or multi-core processing device). Merely by way of example, the processing device 120 may include a central processing unit (CPU), a specialized integrated circuit (ASIC), a specialized instruction processor (ASIP), a graphics processor (GPU), a physical processor (PPU), a digital signal processor (DSP), a field programmable gate array (FPGA), a programmable logic circuit (PLD), a controller, a microcontroller unit, a reduced instruction set computer (RISC), a microprocessor, or the like, or any combination thereof.

In some embodiments, the processing device 120 may be a single server or a server group. The server group may be centralized or distributed. In some embodiments, the processing device 120 may be local or remote. Merely for illustration, only one processing device 120 is described in the noise analysis system 100. However, it should be noted that the noise analysis system 100 in the present disclosure may also include multiple processing devices. Thus operations and/or method steps that are performed by one processing device 120 as described in the present disclosure may also be jointly or separately performed by the multiple processing devices. For example, if in the present disclosure the processing device 120 of the noise analysis system 100 executes both process A and process B, it should be understood that the process A and the process B may also be performed by two or more different processing devices jointly or separately in the noise analysis system 100 (e.g., a first processing device executes process A and a second processing device executes process B, or the first and second processing devices jointly execute processes A and B).

The storage device 130 may store data or information generated by other devices. In some embodiments, the storage device 130 may store data and/or information collected by the medical imaging device 110, such as the plurality of signals of the target object, or the like. In some embodiments, the storage device 130 may store data and/or information processed by the processing device 120, such as the signal ratio, the noise parameter, the corrected signals, or the like. The storage device 130 may include one or more storage components, and each component may be an independent device or a part of other devices. The storage device may be local or implemented through cloud platforms.

The terminal 140 may enable a user interaction with other components in the noise analysis system 100. For example, a doctor may issue operating instructions to the medical imaging device 110 through the terminal 140 to enable the medical imaging device 110 to complete designated operations, such as obtaining the signals of the target object, etc. In some embodiments, the terminal 140 may send control instructions to the processing device 120 to instruct the processing device 120 to perform noise analysis methods illustrated in some embodiments of the present disclosure. In some embodiments, the terminal 140 may receive the corrected signals (e.g., a noise reduction image) from the device processing 120 and display information (e.g., a reconstructed image) to the user. The user may determine a current state of a patient based on the corrected signals to perform effective and targeted examination and/or treatment for the patient. In some embodiments, the terminal 140 may be one or any combination of other devices with input and/or output functions, such as a mobile device 140-1, a tablet computer 140-2, a laptop computer 140-3, a desktop computer, or the like.

The network 150 may connect various other components of the noise analysis system 100 and/or connect other components of the noise analysis system 100 with external devices. The network 150 may enable the connected components to exchange data and/or information. In some embodiments, one or more components in the noise analysis system 100 (e.g., the medical imaging device 110, the processing device 120, the storage device 130, the terminal 140, etc.) may send the data and/or information to other components through the network 150. In some embodiments, the network 150 may include a wired networks or a wireless network.

It should be noted that the above description of the noise analysis system 100 is merely provided for the purposes of illustration, and not intended to limit the scope of the present disclosure. For persons having ordinary skills in the art, multiple variations and modifications may be made under the teachings of the present disclosure. The features, structures, methods, and other features of the exemplary embodiments described in the present disclosure can be combined in various ways to obtain additional and/or alternative exemplary embodiments. For example, the processing device 120 may be implemented based on a cloud computing platform, such as a public cloud, a private cloud, a community, or a hybrid cloud. However, those variations and modifications do not depart from the scope of the present disclosure.

Figure 2:
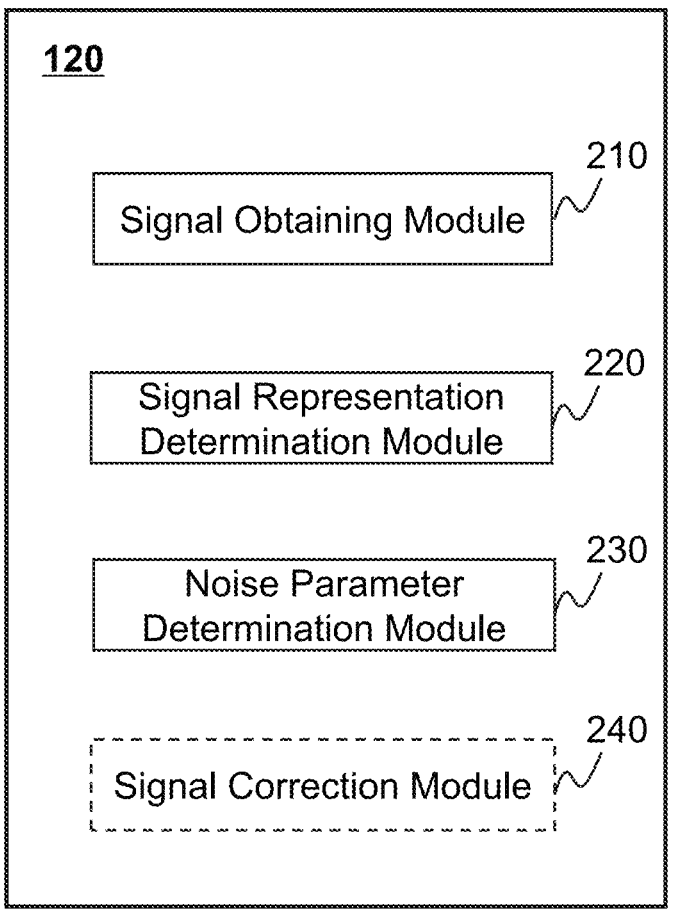
FIG. 2 is a block diagram illustrating exemplary processing device according to some embodiments of the present disclosure.

FIG. 2 is a block diagram illustrating exemplary processing device 120 according to some embodiments of the present disclosure. As shown in FIG. 2, in some embodiments, the processing device 120 may include a signal obtaining module 210, a signal representation determination module 220, and a noise parameter determination module 230.

The signal obtaining module 210 may be configured to obtain information relating to the noise analysis system 100. For example, the signal obtaining module 210 may obtain a plurality of signals of a target object. More descriptions regarding the obtaining of the plurality of signals of the target object may be found elsewhere in the present disclosure. See, e.g., operation 310 in FIG. 3, and relevant descriptions thereof.

The signal representation determination module 220 may be configured to determine a first value of the first signal representation and a second value of the second signal representation of the target object based on the plurality of signals. In some embodiments, the first signal representation and the second signal representation may be defined as reciprocal with respect to each other. More descriptions regarding the determination of the first value of the first signal representation and the second value of the second signal representation of the target object may be found elsewhere in the present disclosure. See, e.g., operation 320 in FIG. 3, and relevant descriptions thereof.

The noise parameter determination module 230 may be configured to determine a value of the noise parameter based on the first value of the first signal representation and the second value of the second signal representation. The noise parameter may reflect an SNR of the plurality of signals. More descriptions regarding the determination of the value of the noise parameter may be found elsewhere in the present disclosure. See, e.g., operation 330 in FIG. 3, and relevant descriptions thereof.

In some embodiments, the processing device 120 may further include a signal correction module 240. The signal correction module 240 may be configured to correct at least one of the first signal and the second signal based on the value of the noise parameter. In some embodiments, at least one of the first signal and the second signal may be corrected based on the value of the noise parameter to obtain a corrected first signal and/or corrected second signal. More descriptions regarding the correction of the first signal and the second signal based on the value of the noise parameter may be found elsewhere in the present disclosure. See, e.g., operation 340 in FIG. 3, and relevant descriptions thereof.

It should be noted that the processing device 120 and the related modules are merely provided for the purposes of illustration, and not intended to limit the scope of the present disclosure. It should be understood that those skilled in the art, after understanding the principle of the system, may arbitrarily combine various modules or form subsystems connected to other modules without deviating from this principle. In some embodiments, the signal obtaining module 210, the signal representation determination module 220, the noise parameter determination module 230, and the signal correction module 240 disclosed in FIG. 2 may be different modules in the same system, or a module that implements the functions of two or more modules mentioned above. For example, the signal representation determination module 220 and the noise parameter determination module 230 may be merged into one module. However, those variations and modifications do not depart from the scope of the present disclosure.

Figure 3:
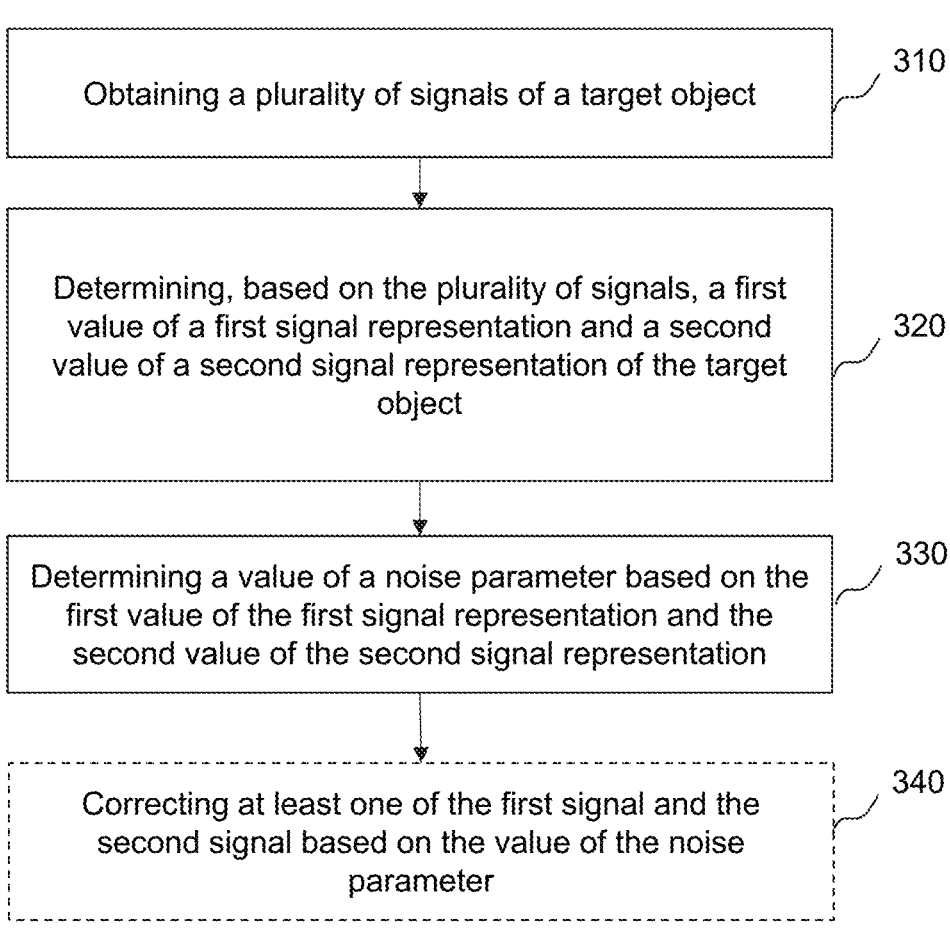
FIG. 3 is a flowchart illustrating an exemplary process for noise analysis according to some embodiments of the present disclosure.

FIG. 3 is a flowchart illustrating an exemplary process for noise analysis according to some embodiments of the present disclosure. In some embodiments, the process 300 may be implemented in the noise analysis system 100 illustrated in FIG. 1. For example, the process 300 may be stored in a storage device (e.g., the storage device 130) as a form of instructions, and invoked and/or executed by the processing device 120 (e.g., one or more modules as illustrated in FIG. 2). The operations of the illustrated process presented below are intended to be illustrative. In some embodiments, the process 300 may be accomplished with one or more additional operations not described, and/or without one or more of the operations discussed. Additionally, the order in which the operations of the process 300 as illustrated in FIG. 3 and described below is not intended to be limiting.

In 310, the processing device 120 (e.g., the signal obtaining module 210) may obtain a plurality of signals of a target object.

The target object refers to an object to be analyzed and/or detected. In some embodiments, the target object may be an object scanned by the medical imaging device 110, such as an organism, a biomimetic model, etc. A signal of an object refers to information that can reflect one or more attributes or features of the object. For example, a signal of the target object may include image data and/or K-space data relating to the target object.

In some embodiments, the plurality of signals of the target object may be obtained by scanning specific tissues, organs, body parts of the target object using the medical imaging device 110 (e.g., an MRI device). For example, the MRI device may be used to apply a magnetic resonance (MR) pulse sequence to the target object to obtain the plurality of signals. The MR pulse sequence may be of various types, such as a spin echo (SE) pulse sequence, a gradient refocused echo (GRE) pulse sequence, an inversion recovery (IR) pulse sequence, a multi-echo MR pulse sequence, a T1ρ-prepared pulse sequence, a T2-prepared pulse sequence, a diffusion weighted imaging (DWI) pulse sequence, etc. In some embodiments, the plurality of signals of the target object may be previously determined by the processing device 120 or another computing device, and stored in a storage device of the noise analysis system 100 (e.g., the storage device 130) or an external source. The processing device 120 may obtain the plurality of signals of the target object from the storage device.

In some embodiments, the plurality of signals of the target object may include a plurality of images of the target object. In some embodiments, the plurality of images of the target object may be registered (or aligned) in image space. In some embodiments, the processing device 120 may determine whether a plurality of initial images of the target object generated based on raw data collected by the MRI device are aligned in image space. In response to determining that the plurality of initial images of the target object are aligned in image space, the processing device 120 may designate the plurality of initial images as the plurality of images of the target object. In response to determining that the plurality of initial images of the target object are not aligned in image space (for example, the initial images correspond to different respiratory phases of the target object), the processing device 120 may perform image registration on the plurality of initial images, and designate the plurality of registered images as the plurality of images of the target object.

In some embodiments, the plurality of signals of the target object may at least include two groups of images, e.g., a first group of images (also referred to as a first signal) and a second group of images (also referred to as a second signal). The processing device 120 may collect the first group of images by instructing an MRI device to perform a first acquisition on the target object, and collect the second group of images by instructing the MRI device to perform a second acquisition on the target object.

In some embodiments, each of the plurality of signals of the target object may correspond to a set of values in a plurality of signal dimensions of signal acquisition using the MRI device. As used herein, a signal dimension of a signal may refer to a parameter that describes an instance under which the signal is determined or acquired using the MRI device. In some embodiments, the plurality of signal dimensions may include an echo time (TE), a unit repetition time (TR), an inversion time (TI), a b-value, a T1ρ-preparation duration, a T2-preparation duration, a repetition, a velocity encoding value, a count of radio frequency (RF) channels, a flip angle, an RF center frequency, an RF receiving coil unit, or the like, or any combination thereof. Merely by way of example, a signal A of the target object may be an image reconstructed based on an echo signal detected by the MRI device during a scan of the target object. The signal dimensions corresponding to the signal A may include, for example, one or more parameters relating to the MRI device during the scan of the target object. Exemplary parameters relating to the MRI device during the scan may include one or more parameters relating to the MR pulse sequence applied during scan, one or more parameters relating to a gradient field or radio frequency field applied during scan, one or more other imaging parameters of the MRI device, or the like, or any combination thereof. The parameter(s) relating to the MR pulse sequence applied during scan may include a TE, a TR, a TI, a b-value, a T1ρ-preparation duration, a T2-preparation duration, a count of repeated collection (i.e., a repetition), a velocity encoding value, or the like. The parameter(s) relating to the gradient field or the radio frequency field applied during scan may include a flip angle, an RF center frequency, or the like. Other imaging parameters of the MRI device may include a count (or number) of RF channels, a coil unit (also referred to as a coil channel), or the like. In some embodiments, the signal dimensions may include at least one or a combination of the TE, the flip angle, the count of repeated collection, or the TI.

In some embodiments, values of the first acquisition and the second acquisition in a first target signal dimension may be different, that is, the first group of images and the second group of images may correspond to different values in the first target signal dimension. For example, the first group of images may correspond to a value V1 in the first target signal dimension and the second group of images may correspond to a value V2 in the first target signal dimension. In some embodiments, the first target signal dimension may include a repetition dimension, and the first acquisition and the second acquisition may be performed by applying a same pulse sequence to the target object in different scans, i.e., repeatedly scanning the target object to obtain the first group of images and the second group of images. At this time, the values of the first acquisition and second acquisition in the repetition dimension may be different. In some embodiments, the first target signal dimension may be an TE dimension, and the first acquisition and the second acquisition may be performed by applying a multi-echo sequence to the target object in a single scan. Specifically, the MRI device may apply the multi-echo sequence to the target object, the first group of images may be obtained by performing the first acquisition at a first echo time, and the second group of images may be obtained by performing the second acquisition at a second echo time. At this time, the values of the first acquisition and the second acquisition in the echo time dimension may be different.

In some embodiments, the first group of images may include a plurality of first images correspond to different values in at least one second target signal dimension, and the second group of images may include the plurality of second images correspond to different values in the at least one second target signal dimension. In some embodiments, the MRI device may include a plurality of coil channels (e.g., a plurality of coil channels contained in multi-channel phased array coils), the at least one second target signal dimension at least include the coil channel dimension. The first group of images may include a plurality of first images collected by the coil channels, the second group of images may include a plurality of second images collected by the coil channels. For example, the second target signal dimension is a coil channel dimension, and the MRI device may use the multi-channel phase array coils to collect the plurality of signals, wherein the multi-channel phase array coils may include i coil channels. The first group of images (which may be recorded as $S_1$) may include the plurality of first images collected by the i coil channels, and the second group of images (which may be recorded as $S_2$) may include the plurality of second images collected by the i coil channels. $S_1$ and $S_2$ may be expressed by $S_{1i}$ and $S_{2i}$, wherein $i \in [1, N1]$, i denotes a serial number of the coil channel and $N_1$ denotes a count of the coil channels. In other words, each of $S_1$ and $S_2$ may be a collection of images collected from N coil channels, i.e., $S_1 = \{S_{11}, S_{12}, \ldots S_{1N}\}$, and $S_2 = \{S_{21}, S_{22}, \ldots S_{2N}\}$.

In some embodiments, the at least one second target signal dimension may further include one or more of the signal dimensions as set forth above other than the first target signal dimension and the coil channel dimension. For example, the at least one second target signal dimension may further include a TE dimension, a repetition dimension, a TR dimension, a TI dimension, a b-value dimension, a T1ρ-preparation duration dimension, a T2-preparation duration dimension, or the like, or any combination thereof. For brief, the coil channel dimension may be referred to as a basic second target signal dimension, and other second target signal dimensions other than the coil channel dimension may be referred to as reference second target signal dimensions. In this case, the first group of images may include a plurality of first images corresponding to different values in one or more reference second target signal dimensions collected by the coil channels, the second group of images may include a plurality of second images corresponding to different values in the one or more reference second target signal dimensions collected by the coil channels. Merely by way of example, the second target signal dimension include the coil channel dimension and a TE dimension, and the MRI device may use the multi-channel phase array coils to collect the plurality of signals, wherein the multi-channel phase array coils may include i coil channels. The first group of images (which may be recorded as $S_1$) may include the plurality of first images collected by the i coil channels, and the second group of images (which may be recorded as $S_2$) may include the plurality of second images collected by the i coil channels. $S_1$ and $S_2$ may be expressed by $S_{1ij}$ and $S_{2ij}$, wherein $i \in [1, N1]$, $j \in [1, N2]$, i denotes a serial number of the coil channel, N1 denotes a count of the coil channels, j denotes a serial number of the echo, and N2 denotes a count of the echoes. In other words, each of $S_1$ and $S_2$ may be a collection of images collected from N1 coil channels, i.e., $S_1 = \{S_{111}, S_{121}, \ldots, S_{112}, S_{122}, \ldots S_{1N1N2}\}$, and $S_2 = \{S_{211}, S_{221}, \ldots, S_{212}, S_{222}, \ldots S_{2N1N2}\}$.

In some embodiments, the plurality of first images and the plurality of second images may be complex images. A pixel value in a complex image may be a complex number, which includes a real part (or a signal amplitude) and an imaginary part (or a signal phase). In some embodiments, the plurality of first images and the plurality of second images may be real images. A pixel value in a real image may be a real number. For example, the complex images may be reconstructed based on the magnetic resonance signals collected by the first acquisition and the second acquisition, and the real images may be generated based on the complex images.

In some embodiments of the present disclosure, a plurality groups of signals may be obtained based on multiple values in the target signal dimension, and a signal intensity of the plurality groups of signals may be equivalent to a noise variance of the plurality groups of signals, which may obtain signals that can effectively reflect the noise variance. In addition, in some embodiments, the noise analysis may be performed on the two consecutive echo images collected from a same excitation, which can avoid performing multiple scans repeatedly and improve the imaging efficiency. There is a difference in signal strength between two echo images collected from the same excitation due to attenuation effect, and the difference may be superimposed as the signal intensity into the noise variance, causing an error in the SNR calculation, therefore conventional SNR calculation approaches cannot perform analysis on the two echo images collected from the same excitation.

In 320, the processing device 120 (e.g., the signal representation determination module 220) may determine, based on the plurality of signals, a first value of the first signal representation and a second value of the second signal representation of the target object. The first signal representation and the second signal representation may be defined as reciprocal with respect to each other.

As used herein, a signal representation of the target object may refer to a representative value or an attribute value of the plurality of signals of the target object. The signal representation of the target object may reflect one or more physiological characteristics or physical characteristics of the target object, which may provide a basis for medical diagnosis and/or treatment.

In some embodiments, a signal representation may be determined by performing specific operations on all or a portion of the plurality of signals. The specific operations may include one or more processing operations, such as a linear operation (e.g., addition, subtraction, multiplication, division, etc.), a nonlinear operation (e.g., an exponential operation, an exponential operation, a logarithmic operation, etc.), or the like, or any combination thereof.

In some embodiments, the first signal representation may be a ratio of the first signal to the second signal, the second signal representation may be a ratio of the second signal to the first signal. In some embodiments, the first value of the first signal representation may be an absolute value of the first signal representation, i.e., a first signal ratio. The second value of the second signal representation may be an absolute value of the second signal representation, i.e., a second signal ratio. Merely by way of example, for the above first signal $S_1$ and second signal $S_2$, $R_1$, and $R_2$ may represent the first value of the first signal representation and the second value of the second signal representation, respectively, and, $R_1 = |S_1/S_2|$, $R_2 = |S_2/S_1|$, that is, the first signal representation and the second signal representation are defined as reciprocal with respect to each other.

In some embodiments, the MRI device may include N coil channels, the first signal $S_1$ may be a collection of the first images collected by the N coil channels, and the second signal $S_2$ may be a collection of the second images collected by the N coil channels, e.g., $S_1=\{S_{11}, S_{12}, \ldots S_{1N}\}$, $S_2=\{S_{21}, S_{22}, \ldots S_{2N}\}$. The first value of the first signal representation and the second value of the second signal representation may be determined using a multiple dimensional integration (MDI) algorithm. The MDI algorithm may integrate the plurality of signals that have different values in the one or more signal dimensions. As set forth above, the first signal and the second signal may include the first group of images and the second group of images, and the values of the first group of images and the second group of images may be different in the target signal dimension. The first signal and the second signal may be processed jointly by using the MDI algorithm. Compared with processing different signals independently, by using the MDI algorithm, the efficiency and/or accuracy of the determination of signal representations may be improved. In some embodiments, the MDI algorithm may integrate information (e.g., summation) in a specific signal dimension (e.g., the coil unit dimension).

In some embodiments, the processing device 120 may determine the first value of the first signal representation and the second value of the second signal representation using the MDI algorithm by performing the following operations. For each coil channel, the processing device 120 may determine a first product of a conjugate image of the second image corresponding to the coil channel and the first image corresponding to the coil channel, e.g., $S^*_{2i}S_{1i}(i \in [1, N 1]$, representing a coil channel serial number). The processing device 120 may also determine a second product of a conjugate image of the first image corresponding to the coil channel and the second image corresponding to the coil channel, e.g., $S^*_{1i}S_{2i}$. The processing device 120 may also determine a third product of the conjugate image of the second image corresponding to the coil channel and the second image corresponding to the coil channel, e.g., $S^*_{2i}S_{2i}$. The processing device 120 may also determine a fourth product of the conjugate image of the first image corresponding to the coil channel and the first image corresponding to the coil channel, e.g., $S^*_{1i}S_{2i}$. Further, the processing device 120 may determine a ratio of a sum of the first products of the plurality of coil channels to a sum of the third products of the plurality of coil channels, and designate the ratio as the first value of the first signal representation. The processing device 120 may also determine a ratio of a sum of the second products of the plurality of coil channels to a sum of the fourth products of the plurality of coil channels, and designate the ratio as the second value of the second signal representation. For example, the second target signal dimension may be the coil channel dimension, and the first value $R_1$ of the first signal representation and the second value $R_2$ of the second signal representation may be calculated according to Equations (1) and (2) as below:

$$R1 = |S1/S2| = \left| \frac{\sum_i S^*_{2i}S_{1i}}{\sum_i S^*_{2i}S_{2i}} \right|, \tag{1}$$

$$R2 = |S2/S1| = \left| \frac{\sum_i S^*_{1i}S_{2i}}{\sum_i S^*_{1i}S_{1i}} \right|, \tag{2}$$

where, $\|$ denotes an operation of taking an absolute value, $*$ denotes a conjugate operation, and $\Sigma$ denotes a summation operation.

As another example, the second target signal dimension may include the coil channel dimension, and two reference second target signal dimensions, and the first value $R_1$ of the first signal representation and the second value $R_2$ of the second signal representation may be calculated according to Equations (3) and (4) as below:

$$R1 = \left| S1/S2 \left| \frac{\sum_{i,j,k}^{N_1,N_2,N_3} S^*_{2ijk} \cdot S_{1ijk}}{\sum_{i,j,k}^{N_1,N_2,N_3} S^*_{2ijk} \cdot S_{2ijk}} \right| \right|, \tag{3}$$

$$R2 = |S2/S1| = \left| \frac{\sum_{i,j,k}^{N_1,N_2,N_3} S^*_{1ijk} \cdot S_{2ijk}}{\sum_{i,j,k}^{N_1,N_2,N_3} S^*_{1ijk} \cdot S_{1ijk}} \right|, \tag{4}$$

where, i denotes a serial number of a value in the coil channel dimension, $N_1$ denotes a count of the coil channels, j denotes a serial number of a value in one of the two reference second target signal dimensions, N2 denotes a count of the values in the one of the two reference second target signal dimensions, k denotes a serial number of a value in the other of the two reference second target signal dimensions, N3 denotes a count of the values in the other of the two reference second target signal dimensions.

According to the Equations (1) and (2), or Equations (3) and (4), although the first signal representation and the second signal representation are defined as reciprocal with respect to each other, the mathematical expressions and the numerical values (i.e., the first value and the second value) of first signal representation and the second signal representation determined according to the MDI algorithm may not be reciprocal with respect to each other. During the determination of the first value of the first signal representation and the second value of the second signal representation by using the MDI algorithm, the first signal and the second signal may be processed jointly, and information integration may be performed in the coil channel dimension (e.g., by adding the first products and second products corresponding to different coils), which can effectively improve the accuracy of the determination of the first signal representation and the second signal representation.

In 330, the processing device 120 (e.g., the noise parameter determination module 230) may determine, based on the first value of the first signal representation and the second value of the second signal representation, a value of the noise parameter. In some embodiments, the noise parameter may reflect an SNR of the plurality of signals.

As used herein, a noise parameter of a signal refers to a parameter that can reflect an influence of a noise in the signal on the signal. In some embodiments, the noise parameter of the signal can reflect an SNR of the signal. In addition, since the noise parameter may be determined by analyzing the plurality of signals (e.g., the first group of images and the second group of images) comprehensively, the noise parameter may be regarded as a comprehensive SNR that reflects an overall SNR of the plurality of signals. For example, the larger the noise parameter is, the higher the SNR of the plurality of signals may be. In some embodiments, the processing device 120 may determine a value of the noise parameter of each physical point of the target object. In some embodiments, the noise parameter may be in a form of noise parameter image, such as a noise parameter image 730 in FIG. 7. Each pixel point in the noise parameter image 730 may correspond to a physical point of the target object, and a pixel value of the pixel point may be determined based on the value of the noise parameter at the corresponding physical point.

In some embodiments, the processing device 120 may designate a product of the first value of the first signal representation and the second value of the second signal representation as the value of the noise parameter. Merely by way of example, as set forth above, $R_1$ and $R_2$ may be the first value of the first signal representation and the second value of the second signal representation, respectively, the noise parameter may be recorded as R, then $R=R_1*R_2$.

Figure 9:
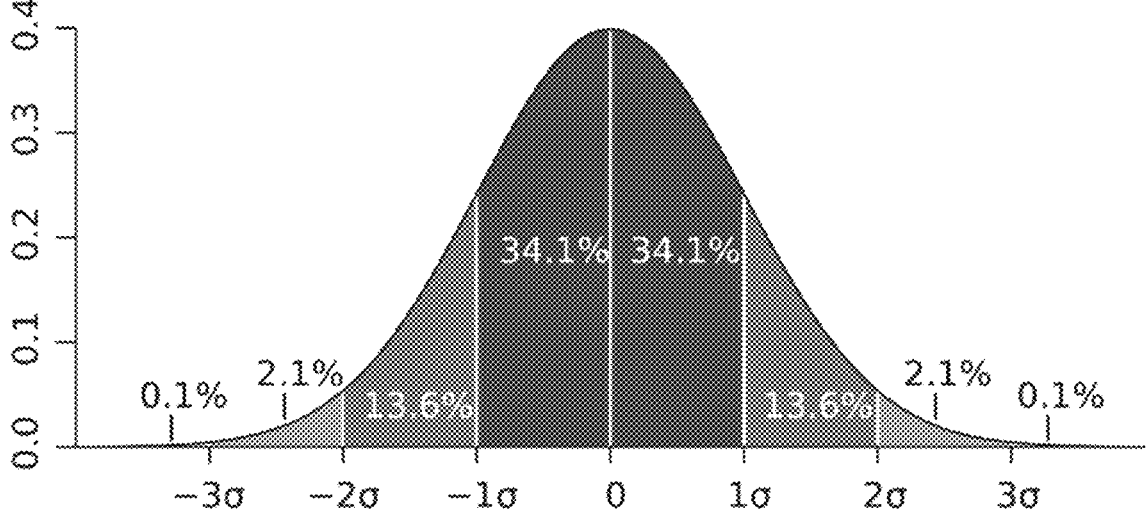
FIG. 9 illustrates an exemplary complex Gaussian distribution noise according to some embodiments of the present disclosure.

In some embodiments, the plurality of signals of the target object may be complex signals (e.g., the complex images). Usually, for the plurality of complex signals, the background noise (also referred to as thermal noise or white noise) may be considered as complex Gaussian noise. If E represents the complex Gaussian distribution noise, a represents a standard deviation of the noise in the plurality of signals, $\varepsilon=\sigma+i\sigma$. Theoretical mean values of the real and imaginary parts of complex Gaussian distribution noise may be both 0, i.e., $\Sigma_\infty\varepsilon=0+i0$. Moreover, there is a 99.73% probability that the values of the real and imaginary parts are randomly distributed within a range of $-3\sigma$ to $+3\sigma$. For example, FIG. 9 illustrates an exemplary complex Gaussian distribution noise according to some embodiments of the present disclosure. As shown in FIG. 9, a horizontal axis represents a strength of the complex Gaussian distribution noise. The mean value of the strength of the complex Gaussian distribution noise may be 0, and there is a 99.73% probability that the strength of the complex Gaussian distribution noise is distributed within the range of $-3\sigma$ to $+3\sigma$.

For example, the first signal $S_1$ and the second signal $S_2$ are magnetic resonance complex signals, and $S_1$ and $S_2$ represent the real signal strengths. If the second target signal dimension includes the coil channel dimension and $S_{1i}+\varepsilon$ and $S_{2i}+\varepsilon$ represent signals of the i-th coil channel with noise, the first value $R_1$ of the first signal representation and the second value $R_2$ of the second signal representation may be determined according to Equations (5) and (6) as below:

$$R1 = \left| \frac{\sum_i (S_{2i}^* + \varepsilon^*)(S_{1i} + \varepsilon)}{\sum_i (S_{2i}^* + \varepsilon^*)(S_{2i} + \varepsilon)} \right|, \quad (5)$$

$$R2 = \left| \frac{\sum_i (S_{1i}^* + \varepsilon^*)(S_{2i} + \varepsilon)}{\sum_i (S_{1i}^* + \varepsilon^*)(S_{1i} + \varepsilon)} \right|, \quad (6)$$

As another example, the first signal $S_1$ and the second signal $S_2$ are magnetic resonance complex signals, and $S_1$ and $S_2$ represent the real signal strengths. If the second target signal dimension includes the coil channel dimension and two reference second target signal dimensions, and $S_{1ijk}+\varepsilon$ and $S_{2ijk}+\varepsilon$ represent signals of the i-th coil channel corresponding to values j and k of the two reference second target signal dimensions with noise, the first value $R_1$ of the first signal representation and the second value $R_2$ of the second signal representation may be determined according to Equations (7) and (8) as below:

$$R_1 = \left| \frac{\sum_{i,j,k}^{N_1,N_2,N_3} \left(S_{2ijk}^* + \varepsilon^*\right)(S_{1ijk} + \varepsilon)}{\sum_{i,j,k}^{N_1,N_2,N_3} \left(S_{2ijk}^* + \varepsilon^*\right)(S_{2ijk} + \varepsilon)} \right|, \quad (7)$$

-continued $$R_2 = \left| \frac{\sum_{i,j,k}^{N_1,N_2,N_3} \left(S_{1ijk}^* + \varepsilon^*\right)(S_{2ijk} + \varepsilon)}{\sum_{i,j,k}^{N_1,N_2,N_3} \left(S_{1ijk}^* + \varepsilon^*\right)(S_{1ijk} + \varepsilon)} \right|, \quad (8)$$

For the plurality of complex signals, if the strengths of the plurality of complex signals are much greater than the noise, that is, the SNR of the plurality of complex signals is high enough, the value of the noise parameter may approach 1. If the strengths of the plurality of complex signals are substantially low and the noise is high enough, the value of the noise parameter may approach 0. For example, according to the Equations (5) and (6), if the SNR of the plurality of complex signals is high enough, i.e., if the strengths of $S_1$ and $S_2$ are much greater than $\varepsilon$, $$R2 \approx \left| \frac{\sum_i S_{2i}^* S_{1i}}{\sum_i S_{2i}^* S_{2i}} \right| = |S2/S1|, \text{ and}$$

$$R1 \approx \left| \frac{\sum_i S_{1i}^* S_{2i}}{\sum_i S_{1i}^* S_{1i}} \right| = |S1/S2|,$$

then $R\approx1$ if the strengths of $S_1$ and $S_2$ is substantially equal to 0, $$R_1 \approx \frac{\pi}{4\sqrt{N}}, \text{ and}$$

$$R_2 \approx \frac{\pi}{4\sqrt{N}},$$

wherein N denotes a count of the coil units of the MRI device. Therefore, as the count of coil units increases, R will approach 0.

Figure 5:
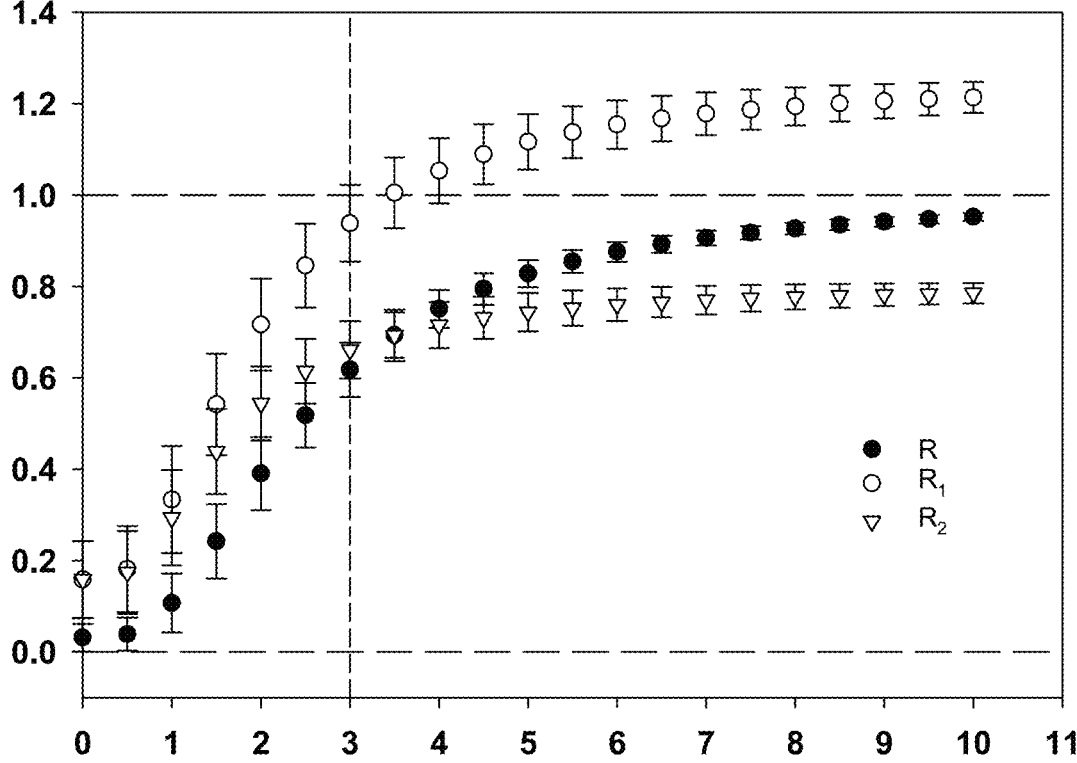
FIG. 5 is a schematic diagram illustrating a relationship between a noise parameter and an SNR according to some embodiments of the present disclosure.

FIG. 5 is a schematic diagram illustrating a relationship between a noise parameter and an SNR according to some embodiments of the present disclosure. The schematic diagram may be obtained through computer simulation. In FIG. 5, a horizontal axis represents the SNR, and a vertical axis represents the noise parameter. As shown in FIG. 5, when the SNR gradually increases from 0, the value of R may rapidly increase and approach 1. Assuming that, in FIG. 5, a first signal strength and a second signal strength are $S_1$ and $S_2$, $S_1=1.25*S2$ (i.e., $S_2=0.8 S_1$). When the SNR is relatively high, $R_1$ may approach 1.25, and $R_2$ may approach 0.8; when the SNR is relatively low, $R_1$, $R_2$, and R may approach 0. In some embodiments, an SNR threshold may be set to 3, which can use as a simple criterion for determining whether the SNR is sufficient, wherein that the SNR is 3 may indicate that the signal intensity is three times the noise variance. When the SNR is greater than 3, the SNR of the signals may be considered as satisfying certain requirements. As shown in FIG. 5, it can be seen that when the SNR is equal to 3, R may approach 0.95, and a noise parameter threshold may be set to 0.95. When the noise parameter is greater than 0.95, the SNR of the signals may be considered as satisfying certain requirements. It should be noted that FIG. 5 is provided for illustrative purposes only. The SNR threshold and/or the noise parameter threshold may be set according to actual requirements.

According to some embodiments of the present disclosure, the noise parameter may be determined based on the plurality of signals in the plurality of signal dimensions of signal acquisition, which may solve the problem that effective signals are difficult to obtain in noise analysis.

According to some embodiments of the present disclosure, noise analysis may be performed on complex signals directly, for example, using the MDI algorithm. Conventional noise analysis approaches perform noise analysis on the real signals converted from complex signals. However, the conversion of signals may change the noise performance, which may reduce the accuracy of noise analysis and increase the difficulty of noise analysis. Some embodiments of the present disclosure may eliminate the need for such signal conversion on the noise analysis, which can improve the accuracy of noise analysis and reduce the difficulty of noise analysis.

According to some embodiments of the present disclosure, the two signal representations (i.e., the first signal representation and the second signal representation) may be represented as ratios of the two signals and may be defined as reciprocal with respect to each other, and the noise parameter may be obtained by simply calculating and multiplying absolute values of the two signal representations, the implementation process is simple, which can avoid the effect of complex calculation on noise performance, and reduce the difficulty of noise analysis. Since the two signal representations are reciprocal to each other, the noise parameter may approach 1 when the noise is low enough and the noise parameter may approach 0 when the noise is high enough, the noise parameter represents a relative magnitude of the noise variance against signal intensity, the noise parameter may be in good agreement with the actual result, which can improve the accuracy of the noise parameter greatly, which effectively eliminates the adverse effects of noise on the magnetic resonance image and improve the image quality.

In addition, in some embodiments of the present disclosure, the effective noise analysis may be performed on two signals consecutively collected from the same excitation, which can reduce the complexity of signal collection, improve the efficiency of signal collection, and reduce the difficulty of noise analysis. Moreover, in some embodiments of the present disclosure, when the noise parameter is determined, a disturbance signal does not need to be introduced, which can reduce the operation difficulty and simplify the analysis process.

In some embodiments, after the operation 330 is performed, the process 300 may further include an operation 340.

In 340, the processing device 120 (e.g., the signal correction module 240) may correct at least one of the first signal and the second signal based on the value of the noise parameter.

In some embodiments, at least one of the first signal and the second signal may be corrected based on the value of the noise parameter to obtain a corrected first signal and/or corrected second signal. For example, the value of the noise parameter at each physical point in the target object may be determined and represented by a noise parameter image. The processing device 120 may multiply the first signal (e.g., a first image) and the noise parameter image to correct the first signal, and/or multiply the second signal (e.g., a second image) and the noise parameter image to correct the second signal. In some embodiments, a correction mask for suppressing noise may be determined based on the value of the noise parameter. The correction mask may be an image obtained according to the noise parameter image and a preset noise parameter threshold. For example, the noise parameter threshold (e.g., 0.6) may be preset. If a pixel point in the noise parameter image (e.g., the noise parameter image 730 in FIG. 7) has a noise parameter R greater than or equal to the noise parameter threshold, a pixel value of the pixel point may be set to 1; if a pixel point in the noise parameter image has a noise parameter R smaller than the noise parameter threshold, a pixel value of the pixel point may be set to 0. In this way, an image obtained after processing all the pixel points in the noise parameter image may be used as the correction mask. In some embodiments, the pixel value of each pixel point in an original image reconstructed using the plurality of signals may be replaced by the noise parameter value of the pixel point to obtain the noise parameter image. For example, the values of the pixel points in the original images S1 and/or S2 may be replaced by the noise parameter R to obtain the noise parameter image. In some embodiments, the original image may be corrected by applying the correction mask to the original image.

In some embodiments, the first signal and/or the second signal may be processed to generate a processed first signal and/or processed second signal, and the processed first signal and/or processed second signal may be corrected based on the value of the noise parameter. Merely by way of example, the first signal may include a plurality of MRI images collected by the plurality of coil channels. The processing device 120 may combine the plurality of MRI images into a combined MRI image, and the combined MRI image may be corrected based on the value of noise parameter (e.g., by multiplying the combined MRI image with the correction mask).

In some embodiments, a third signal different from the first signal and the second signal may be corrected based on the value of the noise parameter calculated based on the first signal and the second signal. For example, the third signal may be an image collected during another scan of the target object other than the first acquisition and the second acquisition using the MRI device or the combined MRI image. The noise parameter image may be obtained based on the first signal and the second signal, and the third signal (e.g., a third image) may be multiplied with the noise parameter image to correct the third signal. As another example, the third signal may be corrected by using the correction mask obtained based on the first signal and the second signal.

In some embodiments, the quality of the plurality of signals of the target object may be evaluated based on the value of noise parameter. For example, for two echo images (e.g., images 610 and 620 shown in FIG. 6) of the target object collected through a dual echo GRE sequence, the noise parameter threshold may be set to 0.95. A noise parameter image (e.g., the noise parameter image 730 shown in FIG. 7) may be obtained based on the two echo images, if a noise parameter R of a pixel point in the noise parameter image is greater than or equal to 0.95, it may indicate that the SNR of the pixel point satisfies requirements and the quality of MR signals of a physical point corresponding to the pixel point may be relatively high. If a noise parameter R of a pixel point on the noise parameter image is smaller than 0.95, it may indicate that the SNR of the pixel point does not satisfy the requirements and the quality of signals of a physical point corresponding to the pixel point may be relatively low. For the two echo images, the more the pixel points that the SNR satisfies the requirements are, the higher the quality of the two echo images may be. If the proportion of pixel points whose SNRs do not satisfy the requirements is greater than or equal to a specific threshold, such as 30%, it may indicate that the quality of the two echo images does not satisfy the requirements, the noise reduction may be performed on the two echo images or the two echo images may be reobtained.

In some embodiments, the noise parameter may be obtained based on a plurality of groups of images (i.e., a plurality of signals). In some embodiments, the strengths of different groups of images may be the same or different. For example, the strengths of two groups of images obtained by scanning the target object twice using the same scan sequence may be the same. As another example, the strengths of different echo images obtained using a multi-echo acquisition sequence may be different. In some embodiments, types of the different groups of images may be the same (e.g., all are T1) or different (e.g., T1 and PD, respectively). In some embodiments, the plurality of groups of images may be complex signals or real signals.

In some embodiments, as described in operation 330, the noise parameter may be regarded as a comprehensive SNR that reflects an overall SNR of the plurality of signals. An accuracy of a reference result determined based on the plurality of signals of the target object may be evaluated based on the value of noise parameter. For example, the reference result may be a parametric map relating to a quantitative parameter of the target object (e.g., a T2* map, an R2* map, etc.). The closer the value of noise parameter is to 1, the higher the quality of the plurality of signals may be and the higher the accuracy of the reference result may be. Merely by way of example, the noise parameter may be in the form of a noise parameter image including a value of the noise parameter of each physical point of the target object, if more than a certain percentage (e.g., 60%) of the physical points has a value of noise parameter smaller than the noise parameter threshold, the processing device 120 may determine that the accuracy of the reference result does not satisfy requirements. In some embodiments, the processing device 120 may perform a noise reduction on the plurality of signals to obtain a plurality of noise reduction signals, and generate a new reference result determined based on the plurality of noise reduction signals.

It should be noted that the process 300 is merely provided for the purposes of illustration, and not intended to limit the scope of the present disclosure. For persons having ordinary skills in the art, multiple variations and modifications may be made for the process 300 under the teachings of the present disclosure. However, those variations and modifications do not depart from the scope of the present disclosure.

Figure 4:
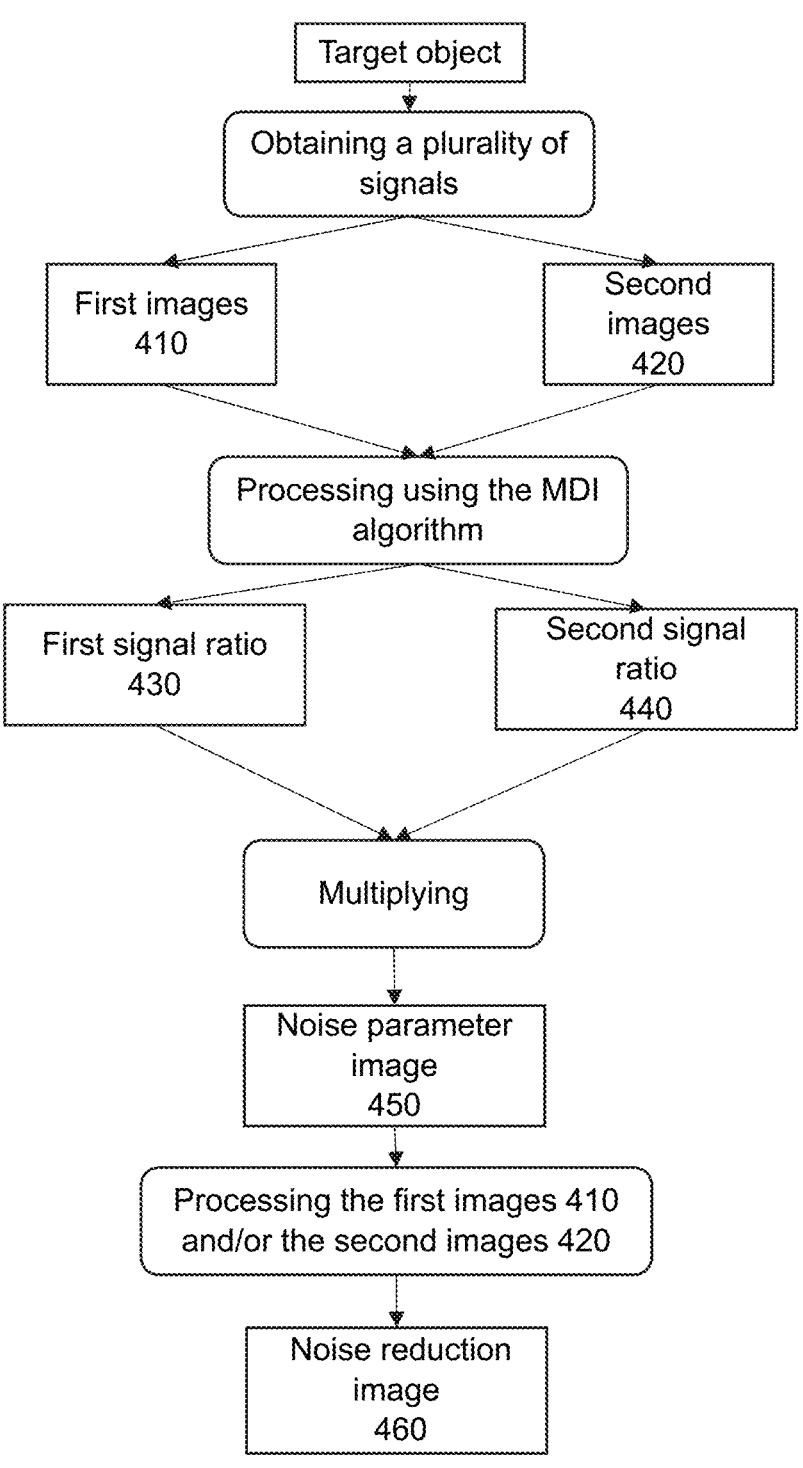
FIG. 4 is a schematic diagram illustrating an exemplary noise analysis process according to some embodiments of the present disclosure.

FIG. 4 is a schematic diagram illustrating an exemplary noise analysis process according to some embodiments of the present disclosure.

Figure 6:
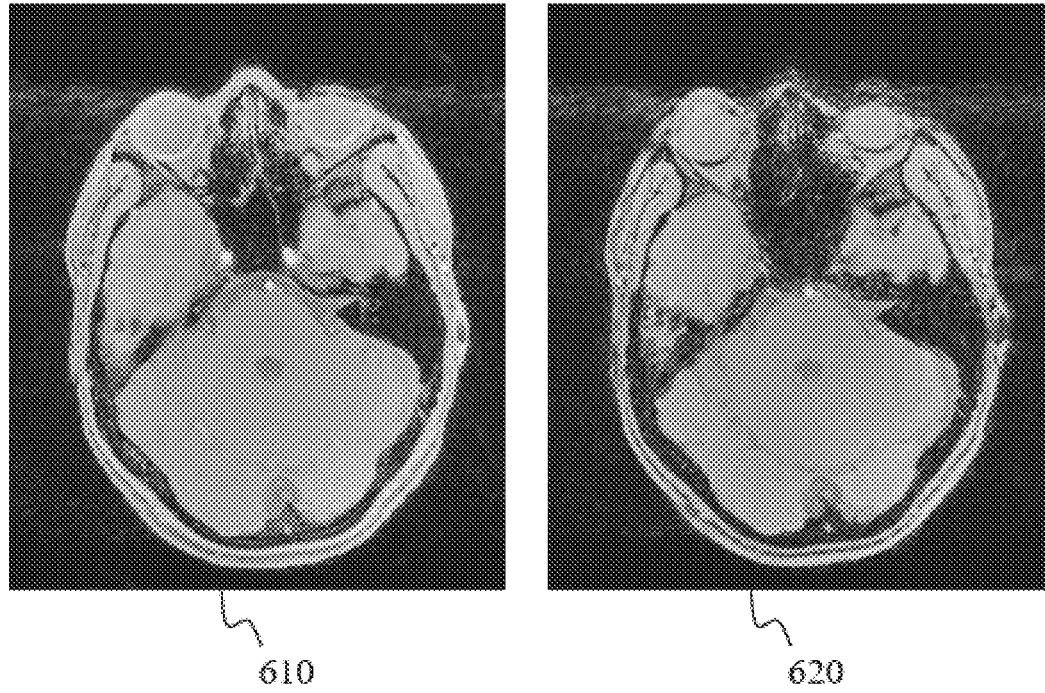
FIG. 6 illustrates an exemplary first image and an exemplary second image according to some embodiments of the present disclosure.

As illustrated in FIG. 4, the processing device 120 may obtain a plurality of signals of a target object. The plurality of signals of the target object may at least include a first signal and a second signal. As shown in FIG. 4, the first signal may include first images 410, and the second signal may include second images 420. Merely by way of example, FIG. 6 illustrates an exemplary first image 610 and an exemplary second image 620 according to some embodiments of the present disclosure. The first image 610 and the second image 620 may be two set of echo images acquired by scanning the brain of the target object using a dual echo GRE sequence. The values of the first image 610 and the second image 620 in the echo time dimension (i.e., the target signal dimension) may be different.

Figure 7:
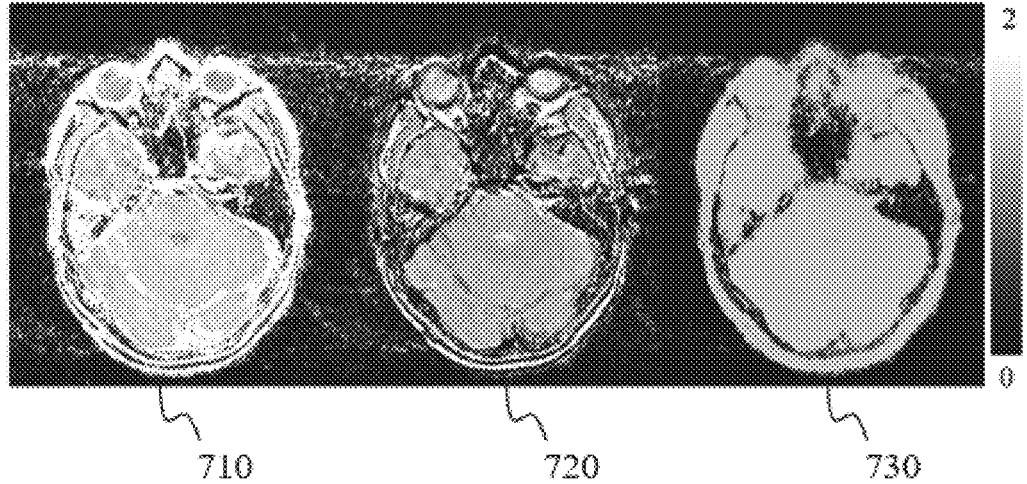
FIG. 7 illustrates an exemplary first signal ratio image, an exemplary second signal ratio image, and an exemplary noise parameter image according to some embodiments of the present disclosure.

The processing device 120 may analyze the first signal and the second signal using the MDI algorithm to obtain a first value of a first signal representation and a second value of a second signal representation of the target object. As shown in FIG. 4, the processing device 120 may obtain a first signal ratio 430 and a second signal ratio 440 by processing the first images 410 and the second images 240 using the MDI algorithm. For example, the first signal ratio 430 may be an absolute value of a ratio of the first signal to the second signal determined based on Equation (1) as aforementioned, and the second signal ratio 440 may be an absolute value of a ratio of the second signal to the first signal determined based on the Equation (2) as aforementioned. In some embodiments, the first signal ratio 430 and the second signal ratio 440 may be represented as images. Merely by way of example, FIG. 7 illustrates an exemplary first signal ratio image 710, an exemplary second signal ratio image 720, and an exemplary noise parameter image 730 according to some embodiments of the present disclosure.

The processing device 120 may determine a noise parameter image 450 by multiplying the first signal ratio 430 with the second signal ratio 440. Merely by way of example, as shown in FIG. 7, the noise parameter image 730 may be a product of the first signal ratio image 710 and the second signal ratio image 720.

Figure 8:
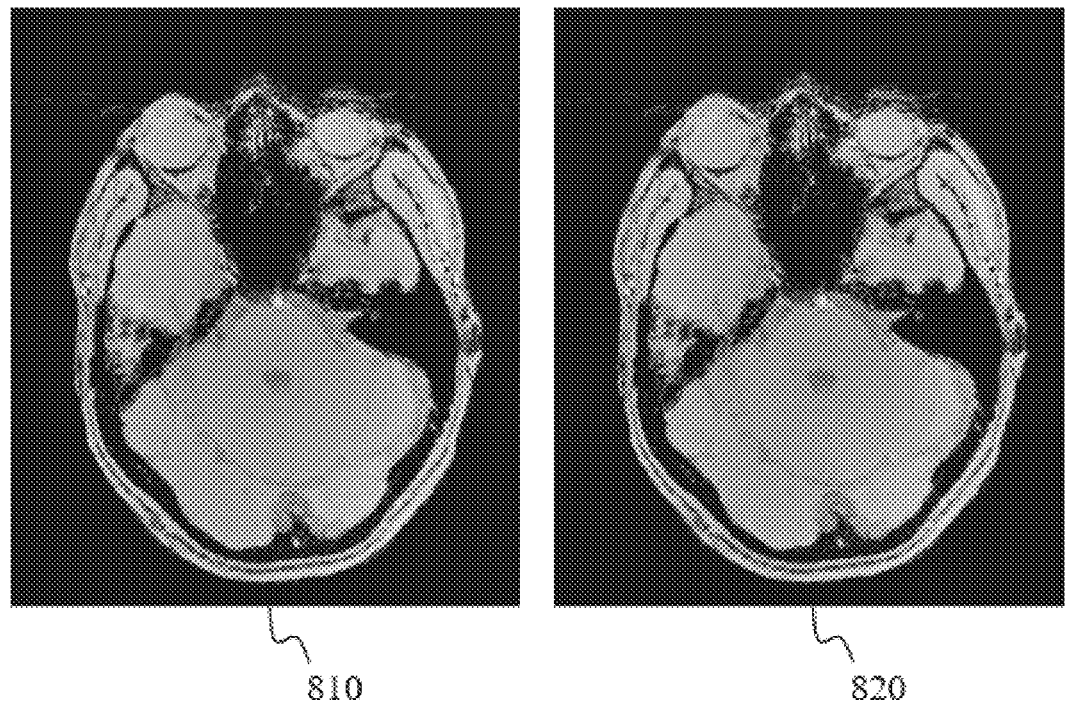
FIG. 8 illustrates exemplary corrected images according to some embodiments of the present disclosure.

The processing device 120 may obtain a noise reduction image 460 by processing the first images 410 and/or the second images 420 based on the noise parameter image 450. The noise reduction image 460 may include at least one of a first noise reduction image obtained by performing a noise reduction on the first images 410 (or a portion thereof) or a second noise reduction image obtained by performing a noise reduction on the second images 420 (or a portion thereof). For example, FIG. 8 illustrates exemplary corrected images 810 and 820 according to some embodiments of the present disclosure. In FIG. 8, the corrected image 810 in FIG. 8 may be obtained by multiplying the noise parameter image 730 in FIG. 7 and the first image 610 in FIG. 6, and the corrected image 820 in FIG. 8 may be obtained by multiplying the noise parameter image 730 in FIG. 7 and the second image 620 in FIG. 6. As shown in FIG. 8, the background noise may be effectively suppressed, and a transition region between the low SNR region and the high SNR region (e.g., an interface between tissues and the air) may be smooth.

In some embodiments of the present disclosure, by performing noise reduction on an original image using the noise parameter image, an MR image with an improved SNR may be obtained, which effectively eliminates the adverse effects of noise on the MR image and improve the image quality.

It will be apparent to those skilled in the art that various changes and modifications can be made in the present disclosure without departing from the spirit and scope of the disclosure. In this manner, the present disclosure may be intended to include such modifications and variations if the modifications and variations of the present disclosure are within the scope of the appended claims and the equivalents thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an subject oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable. In some embodiments, a classification condition used in classification or determination is provided for illustration purposes and modified according to different situations. For example, a classification condition that "a value is greater than the threshold value" may further include or exclude a condition that "the probability value is equal to the threshold value."

What is claimed is:

1. A method for noise analysis, implemented on at least one processor, comprising:

obtaining magnetic resonance (MR) data of a target object by using a magnetic resonance imaging (MRI) device to apply an MR pulse sequence to the target object;

reconstructing a plurality of MR images of the target object based on the MR data;

determining, based on the plurality of MR images, a first value of a first signal representation and a second value of a second signal representation of the target object, wherein the first signal representation and the second signal representation are defined as reciprocal with respect to each other;

determining a noise parameter image based on the first value of the first signal representation and the second value of the second signal representation, wherein each pixel point in the noise parameter image corresponds to a physical point of the target object, and a pixel value of each pixel point is associated with a value of a noise parameter at its corresponding physical point;

obtaining at least one noise reduction image by correcting at least one of the plurality of MR images based on the noise parameter image; and sending the at least one noise reduction image to a terminal for display.

2. The method of claim 1, wherein the plurality of MR images at least include a first group of images and a second group of images that are collected respectively in a first acquisition and a second acquisition performed by the MRI device.

3. The method of claim 2, wherein the first group of images and the second group of images correspond to different values in a first target signal dimension.

4. The method of claim 3, wherein the first target signal dimension is a repetition dimension, and the first acquisition and the second acquisition are performed by applying a same pulse sequence in different scans.

5. The method of claim 3, wherein the first group of images include a plurality of first images corresponding to different values in one or more reference second target signal dimensions, the second group of images include a plurality of second images corresponding to different values in the one or more reference second target signal dimensions, the one or more reference second target signal dimensions referring to one or more signal dimensions other than the first target signal dimension and a coil channel dimension.

6. The method of claim 2, wherein the first group of images include a plurality of first images corresponding to different values in at least one second target signal dimension, and the second group of images include a plurality of second images corresponding to different values in the at least one second target signal dimension.

7. The method of claim 6, wherein the MRI device includes a plurality of coil channels, and the at least one second target signal dimension at least includes a coil channel dimension.

8. The method of claim 6, wherein the plurality of first images and the plurality of second images are complex images.

9. The method of claim 2, wherein the first signal representation is a ratio of the first group of images to the second group of images, and the second signal representation is a ratio of the second group of images to the first group of images.

10. The method of claim 2, wherein the MRI device includes a plurality of coil channels, the first group of images include a plurality of first MR images respectively collected by the coil channels in the first acquisition, and the second group of images include a plurality of second MR images respectively collected by the coil channels in the second acquisition.

11. The method of claim 10, wherein the first value of the first signal representation is an absolute value of the first signal representation, the second value of the second signal representation is an absolute value of the second signal representation, and the determining, based on the plurality of MR images, a first value of a first signal representation and a second value of a second signal representation of the target object includes:

for each of the plurality of coil channels, determining a first product of a conjugate image of the second image corresponding to the coil channel and the first image corresponding to the coil channel, a second product of a conjugate image of the first image corresponding to the coil channel and the second image corresponding to the coil channel, a third product of the conjugate image of the second image corresponding to the coil channel and the second image corresponding to the coil channel, and a fourth product of the conjugate image of the first image corresponding to the coil channel and the first image corresponding to the coil channel;

designating a ratio of a sum of the first products of the plurality of coil channels to a sum of the third products of the plurality of coil channels as the first value of the first signal representation; and designating a ratio of a sum of the second products of the plurality of coil channels to a sum of the fourth products of the plurality of coil channels as the second value of the second signal representation.

12. The method of claim 1, wherein the determining, based on the plurality of MR images, the first value of the first signal representation and the second value of the second signal representation includes:

determining the first value of the first signal representation and the second value of the second signal representation using a multi-dimensional integration (MDI) algorithm.

13. The method of claim 1, wherein the determining a noise parameter image based on the first value of the first signal representation and the second value of the second signal representation includes:

designating a product of the first value of the first signal representation and the second value of the second signal representation as the noise parameter image.

14. The method of claim 1, wherein the noise parameter image reflects a signal-to-noise ratio (SNR) of the plurality of MR images.

15. The method of claim 1, wherein the at least one of the plurality of images is corrected based on the noise parameter image by:

obtaining a correction mask according to the noise parameter image and a preset noise parameter threshold; and correcting the at least one of the plurality of images by applying the correction mask.

16. The method of claim 1, wherein the obtaining MR data of a target object by using an MRI device to apply an MR pulse sequence to the target object comprises: obtaining first MR data of the target object by using the MRI device to apply the MR pulse sequence on the target object in a first acquisition; and obtaining second MR data of the target object by using the MRI device to apply the MR pulse sequence on the target object in a second acquisition; and the reconstructing a plurality of MR images of the target object based on the MR data comprises: reconstructing a first group of MR images based on the first MR data collected in the first acquisition, and reconstructing a second group of MR images based on the second MR data collected in the second acquisition.

17. The method of claim 1, wherein the MR pulse sequence is a multi-echo sequence, the MR data includes first MR data collected in a first acquisition at a first echo time and second MR data collected in a second acquisition at a second echo time, the reconstructing a plurality of MR images of the target object based on the MR data comprises: reconstructing a first group of MR images based on the first MR data collected in the first acquisition, and reconstructing a second group of MR images based on the second MR data collected in the second acquisition.

18. The method of claim 1, further comprising:

evaluating, based on the noise parameter image, a parametric map relating to a quantitative parameter of the target object.

19. A system for noise analysis, comprising:

at least one storage device including a set of instructions; and at least one processor in communication with the at least one storage device, wherein when executing the set of instructions, the at least one processor is configured to direct the system to perform operations including:

obtaining a plurality of signals of a target object by using a magnetic resonance imaging (MRI) device to apply an MR pulse sequence to the target object;

determining, based on the plurality of signals, a first value of a first signal representation and a second value of a second signal representation of the target object, wherein the first signal representation and the second signal representation are defined as reciprocal with respect to each other;

determining a value of a noise parameter based on the first value of the first signal representation and the second value of the second signal representation;

obtaining at least one noise reduction image by correcting at least one of the plurality of signals based on the noise parameter.

20. A non-transitory computer readable medium, comprising at least one set of instructions for noise analysis, wherein when executed by one or more processors of a computing device, the at least one set of instructions causes the computing device to perform a method, the method comprising:

obtaining magnetic resonance (MR) data of a target object by using a magnetic resonance imaging (MRI) device to apply an MR pulse sequence to the target object;

reconstructing a plurality of MR images of the target object based on the MR data;

determining, based on the plurality of MR images, a first value of a first signal representation and a second value of a second signal representation of the target object, wherein the first signal representation and the second signal representation are defined as reciprocal with respect to each other;

determining a noise parameter image based on the first value of the first signal representation and the second value of the second signal representation, wherein each pixel point in the noise parameter image corresponds to a physical point of the target object, and a pixel value of each pixel point is associated with a value of a noise parameter at its corresponding physical point;

obtaining at least one noise reduction image by correcting at least one of the plurality of MR images based on the noise parameter image; and sending the at least one noise reduction image to a terminal for display.

* * * * *